(12) United States Patent
Guala et al.

(10) Patent No.: US 8,097,578 B2
(45) Date of Patent: Jan. 17, 2012

(54) CONCENTRATED BASE FOR DETERGENT PRODUCTS AND PRODUCTS FOR PERSONAL CARE AND HYGIENE COMPRISING A COMBINATION OF AT LEAST THREE NON-ETHOXYLATED SURFACTANTS

(75) Inventors: Fabrizio Guala, Trino (IT); Elisabetta Merlo, Trino (IT); Giovanni Villa, Paderno Dugnano (IT)

(73) Assignee: Zschimmer & Schwarz Italiana S.p.A., Tricerro (IT)

( * ) Notice: Subject to any disclaimer, the term of this patent is extended or adjusted under 35 U.S.C. 154(b) by 0 days.

(21) Appl. No.: 12/736,432

(22) PCT Filed: Apr. 9, 2009

(86) PCT No.: PCT/IB2009/051503
§ 371 (c)(1),
(2), (4) Date: Oct. 7, 2010

(87) PCT Pub. No.: WO2009/125367
PCT Pub. Date: Oct. 15, 2009

(65) Prior Publication Data
US 2011/0034361 A1  Feb. 10, 2011

(30) Foreign Application Priority Data
Apr. 10, 2008 (IT) ................................ TO08A0277

(51) Int. Cl.
*C11D 17/00* (2006.01)

(52) U.S. Cl. ........ 510/424; 510/426; 510/427; 510/428; 510/490; 510/499

(58) Field of Classification Search .................. None
See application file for complete search history.

(56) References Cited

U.S. PATENT DOCUMENTS

| 5,478,490 | A |   | 12/1995 | Russo et al. |
| 5,696,069 | A | * | 12/1997 | Ito et al. ........................ 510/123 |
| 6,001,787 | A |   | 12/1999 | Pratley |
| 6,030,931 | A |   | 2/2000  | Vinski et al. |
| 2005/0008601 | A1 | | 1/2005  | Ariotto et al. |
| 2006/0257347 | A1 | | 11/2006 | Kim et al. |

FOREIGN PATENT DOCUMENTS
EP  0559375  9/1993

* cited by examiner

*Primary Examiner* — Necholus Ogden, Jr.
(74) *Attorney, Agent, or Firm* — Dykema Gossett PLLC

(57) ABSTRACT

The invention relates to a concentrated base, particularly for detergent products and products for personal care and hygiene, comprising a combination of at least three surfactants selected from the group consisting of acylmethyltaurates, alkylamidopropylbetaines, alkyl amphoacetates, alkyl amphodiacetates, alkylsulphoacetates, acyl sarcosinates, acyl lactylates and acyl glutamates. The viscosity of the concentrated base of the invention can advantageously be adjusted by simple dilution with water to the concentration of use and/or by adding small amounts of electrolytes. Detergent products and products for personal care and hygiene comprising the concentrated base of the invention are also described.

14 Claims, No Drawings

CONCENTRATED BASE FOR DETERGENT PRODUCTS AND PRODUCTS FOR PERSONAL CARE AND HYGIENE COMPRISING A COMBINATION OF AT LEAST THREE NON-ETHOXYLATED SURFACTANTS

The present invention relates to concentrated bases of non-ethoxylated surfactants for detergent products and products for personal care and hygiene.

The recent demands of the marketplace, the requirements of so-called green chemistry, and the various environmental and ecological certifications are increasingly steering the cosmetics market, and in general the market for detergents, towards products obtained from renewable raw materials, possibly of vegetable origin.

The current trend is moreover to avoid the use of raw materials obtained by chemical syntheses that envisage processes of ethoxylation and/or sulphation, since these raw materials have proved excessively aggressive with respect to the skin.

We also try to avoid the use of alkanolamides as viscosity improvers, because of the possible formation of nitrosamines.

These requirements, which are connected both with tolerability and with the environmental compatibility of detergents and cosmetics, mean that in practice the formulator is faced with various difficulties. Without lauryl/laurylethoxysulphates as surfactants, the detergency, foam formation and the viscosity of rinse-off products tend to be unacceptable from the standpoint of the consumer, who is accustomed to products characterized by good cleaning power, excellent foaming power even in hard water and good viscosity, which is generally regarded as synonymous with richness of content.

To satisfy these needs, formulations have been marketed that contain only amphoteric and/or non-ionic surfactants, but have the disadvantage of being very substantive on the skin and hair and have little affinity for the sebum/dirt that they ought to remove. Furthermore, the foam of the non-ethoxylated surfactants has little resistance to hard water. However, there is still the important problem concerning achievement of sufficient viscosity.

In the traditional detergents the problem of providing the product with sufficient viscosity is solved by the use of laurylethoxysulphates/alkylamidopropylbetaines or by means of alkanolamides, which have the disadvantages mentioned above.

Other available viscosity improvers are the synthetic polymers of the carbomer type, though these have the same disadvantages mentioned above in relation to the ethoxylated substances.

Gums (such as for example xanthan gum), which could be used in cosmetics, have a skin feeling that is sometimes unpleasant.

Finally, other anionic surfactants that might be used as viscosity improvers are solid at room temperature and would therefore require hot processes that the formulator cannot always countenance for reasons connected with costs.

The aim of the present invention is to provide a concentrated base of non-ethoxylated surfactants, particularly for detergent products and products for personal care and hygiene, comprising a mixture of surfactants that is easy to formulate, has good washing power, good foaming power and can be adjusted in viscosity by simple dilution with water and, optionally, subsequent addition of small amounts of electrolytes.

Another aim of the present invention is to provide a concentrated base as defined previously, that does not require preservatives and that is gentle on the skin and hair.

These and other aims are achieved by means of a concentrated base as defined in the preamble of Claim 1, comprising a combination of at least three surfactants selected from the group consisting of acylmethyltaurates of formula (I), alkylamidopropylbetaines of formula (II), alkyl amphoacetates of formula (III), alkyl amphodiacetates of formula (IV), alkylsulphoacetates of formula (V), acylsarcosinates of formula (VI), acyl lactylates of formulae (VII) and (VII)' and acylglutamates of formula (VIII), in an aqueous medium. The scope of the invention includes all combinations of at least three surfactants from those stated above.

The total amount of surfactant in the concentrated base of the invention is preferably comprised within the range of 3% to 70% of active substance (AS). Other preferred ranges are 3%-65%, 3%-60%, 4%-70%, 4%-65% or 4%-60% AS.

The pH of the concentrated base of the present invention is preferably between 4.5 and 7.5, even more preferably between 5 and 7, although the preferred value varies depending on the combination of surfactants.

The concentrated base of the present invention displays the advantageous characteristics mentioned above. As will be illustrated in the section relating to the examples, the concentrated base of the invention, when diluted with water and optionally small amounts of electrolytes, is able to form a gel having a viscosity value suitable for the formulation of detergent products and products for personal care and hygiene, for example shampoos, foam baths, foam shower, dishwashing agents, liquid soaps and rinsing products in general.

These final products generally contain, in addition to the concentrated base of the invention diluted with water until the desired viscosity is reached, further active substances and additives of various kinds that are usual for products for personal care and hygiene and for detergents generally, that are selected in relation to the type of final product desired.

The final product can for example include pH regulators, perfumes, colorants, preservatives, antioxidants, moisturizing agents, fluidizing agents, solubilizers, humectants.

For example, the final product can contain glycerol, urea, sorbitol or the like, which perform the function of humectants and moisturizers. The rheological performance can be improved by adding glyceryl oleate, on its own or in combination with an emollient, to the final product.

If the final product requires the addition of perfumes, which generally are oily substances, a person skilled in the art is able to select suitable non-ethoxylated solubilizers, for example alkyl glucosides, alkyl polyglucosides, polyglycerols and/or esterified polyglycerols or other molecules with characteristics similar to the above.

Said additives are well known to a person skilled in the art, who is able to select the type and the quantity of additives required in relation to the desired final product.

The additives can be added to said concentrated base or can be added during preparation of the final product.

The general formulae of the surfactants used in the concentrated base of the invention are as follows:

FORMULA (I): ACYLMETHYLTAURATES

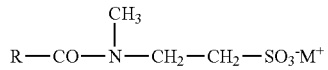

in which R is a linear or branched, saturated or unsaturated alkyl radical, having from 3 to 30 carbon atoms, preferably coco alkyl, and M⁺ is H⁺ or a cation of an organic or inorganic base.

When M⁺ in formula (I) is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When M⁺ in formula (I) is a cation derived from an inorganic base, the inorganic base is preferably KOH, NaOH, NH₃.

FORMULA (II): ALKYLAMIDOPROPYLBETAINES

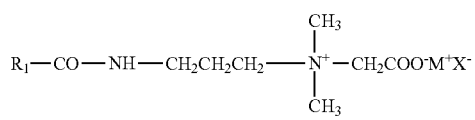

in which $R_1$ is a saturated or unsaturated, linear or branched alkyl radical, having from 3 to 30 carbon atoms, preferably coco alkyl, M⁺ is H⁺ or a cation of an organic or inorganic base, X⁻ is an inorganic or organic anion.

When M⁺ in formula (II) is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When M⁺ in formula (II) is a cation derived from an inorganic base, the inorganic base is preferably KOH, NaOH, NH₃.

The anion X⁻ is preferably a halide anion, preferably the anion Cl⁻.

FORMULA (III): ALKYL AMPHOACETATES

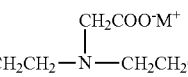

FORMULA (IV): ALKYL AMPHODIACETATES

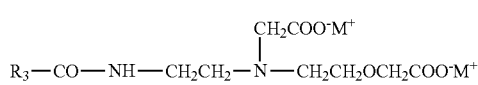

In formulae (III) and (IV), $R_2$ and $R_3$ are, independently of one another, a saturated or unsaturated, linear or branched alkyl radical, having from 3 to 30 carbon atoms, preferably coco alkyl, M⁺ is H⁺ or a cation of an organic or inorganic base.

When M⁺ is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When M⁺ is a cation derived from an inorganic base, the inorganic base is preferably KOH, NaOH, NH₃.

FORMULA (V): ALKYLSULPHOACETATES

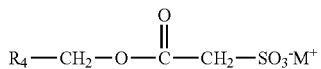

in which $R_4$ is a saturated or unsaturated, linear or branched alkyl radical, having from 3 to 30 carbon atoms, preferably 11 carbon atoms (C11), and M⁺ is H⁺ or a cation of an organic or inorganic base.

When M⁺ in formula (V) is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When M⁺ in formula (V) is a cation derived from an inorganic base, the inorganic base is preferably KOH, NaOH, NH₃.

FORMULA (VI): ACYLSARCOSINATES

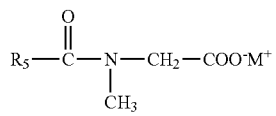

in which $R_5$ is a saturated or unsaturated, linear or branched alkyl radical, having from 3 to 30 carbon atoms, preferably 13 carbon atoms, and M⁺ is H⁺ or a cation of an organic or inorganic base.

When M⁺ in formula (VI) is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When M⁺ in formula (VI) is a cation derived from an inorganic base, the inorganic base is preferably KOH, NaOH, NH₃.

FORMULAE (VII) and (VII)': ACYL LACTYLATES

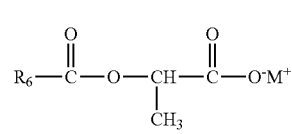
(VII)

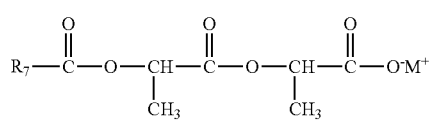
(VII)' in which $R_6$ and $R_7$ are, independently of one another, a saturated or unsaturated, linear or branched alkyl radical, having from 3 to 30 carbon atoms, preferably C11 or C17, and M⁺ is H⁺ or a cation of an organic or inorganic base.

When M⁺ in formula (VIII) or (VIII)' is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When $M^+$ in formula (VIII) or (VIII)' is a cation derived from an inorganic base, the inorganic base is preferably KOH, NaOH, $NH_3$.

FORMULA (VIII): ACYLGLUTAMATES

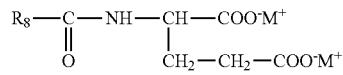

in which $R_8$ is a saturated or unsaturated, linear or branched alkyl radical, having from 3 to 30 carbon atoms, preferably C13, and $M^+$ is $H^+$ or a cation of an organic or inorganic base.

When $M^+$ in formula (IX) is a cation derived from an organic base, the organic base is preferably selected from MIPA (monoisopropanolamine), TIPA (triisopropanolamine), Tris Amino (2-amino-2-hydroxymethyl-1,3-propanediol), AEDP (2-amino-2-ethyl-1,3-propanediol), AMPD (aminomethylpropanediol) and AMP (aminomethylpropanol). Even more preferably, the organic base is AMP. When $M^+$ in formula (IX) is a cation derived from an inorganic base, the inorganic base is preferably KOH, NaOH, $NH_3$.

The examples given below are provided for purposes of illustration only and are not intended to limit the scope of the invention as defined in the appended claims.

Examples 1 to 10 illustrate some concentrated bases that fall within the scope of the present invention. Example 11 describes the foam tests that were carried out. Example 12 describes some detergent products for personal care and hygiene that include the concentrated bases of the present invention.

EXAMPLE 1

Base A

From 1% to 25% of active substance of sodium myristoylsarcosinate of formula (a) below, from 1% to 25% of active substance of cocoamidopropyl betaine of formula (b) below, from 1% to 10% of active substance of sodium laurylsulphoacetate of formula (c) below, water q.s. to 100%. The pH of the concentrated base A is preferably less than or equal to 5.5.

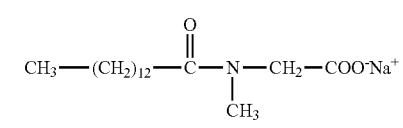

(a)

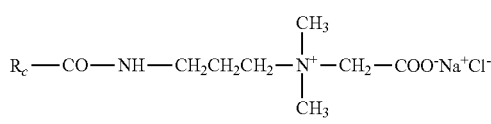

(b)

($R_c$ is the mixture of alkyl radicals derived from coco)

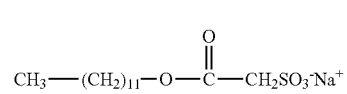

(c)

EXAMPLE 2

Base B

From 1 to 30% of active substance of sodium cocoamphoacetate of formula (d) below, from 1% to 25% of active substance of sodium myristoylsarcosinate of formula (a), from 1% to 10% of active substance of sodium laurylsulphoacetate of formula (c), water q.s. to 100%. The pH of the concentrated base B is preferably less than or equal to 6.2.

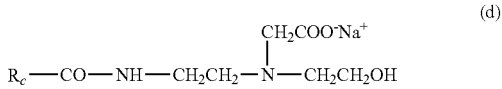

(d)

($R_c$ is the mixture of alkyl radicals derived from coco)

EXAMPLE 3

Base C

From 1% to 25% of active substance of sodium myristoylglutamate of formula (e) below, from 1% to 25% of active substance of cocoamidopropyl betaine of formula (b), from 1% to 10% of active substance of sodium laurylsulphoacetate of formula (c), water q.s. to 100%. The pH of the concentrated base C is preferably less than or equal to 5.0.

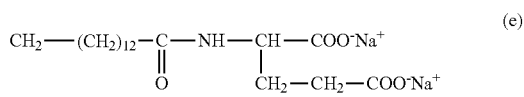

(e)

EXAMPLE 4

Base D

From 1 to 30% of active substance of sodium cocoamphoacetate of formula (d), from 1% to 25% of active substance of sodium myristoylglutamate of formula (e), from 1% to 10% of active substance of sodium laurylsulphoacetate of formula (c), water q.s. to 100%. The pH of the concentrated base D is preferably less than or equal to 5.5.

EXAMPLE 5

Base E

From 1% to 25% of active substance of sodium myristoylglutamate of formula (e), from 1% to 25% of active substance of cocoamidopropyl betaine of formula (b), from 1% to 10% of active substance of sodium myristoylsarcosinate of formula (a), from 1% to 10% of active substance of sodium cocoyl methyltaurate of formula (f) below, water q.s. to 100%. The pH of the concentrated base E is preferably less than or equal to 5.8.

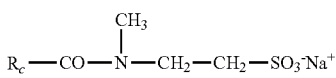

(f)

($R_c$ is the mixture of alkyl radicals derived from coco).

EXAMPLE 6

Base F

From 1 to 30% of active substance of sodium cocoamphoacetate of formula (d), from 1% to 15% of active substance of sodium myristoylglutamate of formula (e), from 1% to 10% of active substance of sodium myristoylsarcosinate of formula (a), from 1% to 10% of active substance of sodium cocoyl methyltaurate of formula (f), water q.s. to 100%. The pH of the concentrated base F is preferably less than or equal to 5.4.

EXAMPLE 7

Base G

From 1% to 25% of active substance of sodium myristoylsarcosinate of formula (a), from 1% to 25% of active substance of cocoamidopropyl betaine of formula (b), from 1% to 15% of active substance of sodium lauroyl lactylate of formula (g) below, water q.s. to 100%. The pH of the concentrated base G is preferably less than or equal to 5.7.

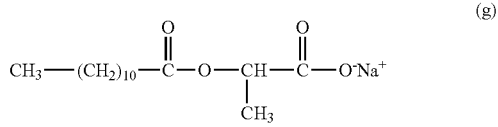

(g)

EXAMPLE 8

Base H

From 1 to 30% of active substance of sodium cocoamphoacetate of formula (d), from 1% to 25% of active substance of sodium myristoylsarcosinate of formula (a), from 1% to 15% of active substance of sodium lauroyl lactylate of formula (g), water q.s. to 100%. The pH of the concentrated base H is preferably less than or equal to 6.8.

EXAMPLE 9

Base I

From 1% to 25% of active substance of sodium myristoyl glutamate of formula (e), from 1% to 25% of active substance of cocoamidopropyl betaine of formula (b), from 1% to 15% of active substance of sodium lauroyl lactylate of formula (g), water q.s. to 100%. The pH of the concentrated base I is preferably less than or equal to 6.2.

EXAMPLE 10

Base L

From 1 to 30% of active substance of sodium cocoamphoacetate of formula (d), from 1% to 25% of active substance of sodium myristoyl glutamate of formula (e), from 1% to 15% of active substance of sodium lauroyl lactylate of formula (g), water q.s. to 100%. The pH of the concentrated base L is preferably less than or equal to 6.5.

EXAMPLE 11

Viscosity and Foaming Power

The bases in Examples 1-10 have viscosity of less than 10000 cP at 20° C. and are therefore easily pumpable.

On diluting with water until we obtain a dry residue equal to 18%—which is the value of dry residue of many foam baths already marketed—a gel is obtained with viscosity greater than 20000 cP at 20° C. On diluting further to 11% of dry residue—which is the value of dry residue of many shampoos already marketed—products are obtained with viscosity greater than 5000 cP at 20° C.

The viscosity of the dilutions depends both on the concentration of surfactants and on the pH value. Generally speaking, it is preferable if the dilutions to approx. 10-20% of the concentrated bases of the invention, including the dilutions to 11% and to 18% mentioned above, have a pH value between 4.5 and 7.5, more preferably between 5 and 7. In particular, the following pH values of the dilutions of the concentrated bases of the present invention are preferred:

dilution of base A: pH greater than or equal to 5.5;
dilution of base B: pH from 5.5 to 6.5;
dilution of base C: pH less than or equal to 5;
dilution of base D: pH less than or equal to 5.5;
dilution of base E: pH less than or equal to 5.5;
dilution of base F: pH less than or equal to 5.4;
dilution of base G: pH less than or equal to 5.5;
dilution of base H: pH less than or equal to 6.7;
dilution of base I: pH less than or equal to 6.2;
dilution of base L: pH less than or equal to 6.6.

In some cases the concentrated base, when diluted, takes on a pearly appearance, which can be a beneficial factor obtainable without the use of the conventional lustre agents.

The foam of the dilutions obtained is compact and creamy. The foam tests were carried out using Base A and Base B of the present invention, as well as the base SLES 2OE (sodium laurylethoxysulphate 2OE) as reference, each diluted to 11% and to 18% of dry residue.

One gram of each dilution was added to 1 liter of hard water (hardness 15° FH), then a volume of 200 ml of this solution in hard water was taken and was used for measurement of the foam. For this purpose, the 200 ml of solution in hard water was put in a cylinder and foam was generated by the use of a perforated plunger (30 strokes in 30 seconds). Finally, the height of the foam that formed in the cylinder was measured.

The results are shown in the following table.

| SLES 2OE D.R. 18% | SLES 2OE D.R. 11% | Base A diluted to D.R. 18% | Base A diluted to D.R. 11% | Base B diluted to D.R. 18% | Base B diluted to D.R. 11% |
|---|---|---|---|---|---|
| 550 ml foam coarse, a little fine | 350 ml foam fine, compact | 450 ml foam fine, compact | 400 ml foam fine, compact | 540 ml foam fine, compact | 330 ml foam fine, compact |

D.R. = dry residue

Base A and Base B used in this test have the following specific composition:

Base A: 14% of active substance of sodium myristoylglutamate, 13% of active substance of cocoamidopropyl betaine and 5% of active substance of lauryl sulphoacetate, water to 100%;

Base B: 8% of active substance of sodium myristoylglutamate, 16% of active substance of sodium cocoamphoacetate, 6% of active substance of lauryl sulphoacetate, glycerol (3%) and urea (2%), water to 100%.

EXAMPLE 12

| Shampoo | |
|---|---|
| Base A according to Example 11 | 30% |
| Sodium cocoyl hydrolysate of grain | 3% |
| Citric acid | q.s. to pH 5.5 |
| Water, perfume, preservatives, excipients | q.s. to 100% |
| Foam shower | |
| Base B according to Example 11 | 40% |
| Lactic acid | q.s. to pH 5.8 |
| Water, colour, preservative and perfume | q.s. to 100% |
| Foam bath | |
| Base E* | 45% |
| Lactic acid | q.s. to pH 5.5 |
| Water, colour, preservative and perfume | q.s. to 100% |
| Shampoo for greasy hair | |
| Base I** | 35% |
| Sodium capryloyl glutamate | 5% |
| Citric acid | q.s. to pH 6.0 |
| Water, perfume, preservatives, excipients | q.s. to 100% |

*Base E: sodium myristoylglutamate 13% of active substance (AS), cocoamidopropyl betaine 12% AS and sodium methyl cocoyl taurate 3% AS, water to 100%;
**Base I: sodium myristoylglutamate 13% AS, cocoamidopropyl betaine 12% AS and sodium lauroyl lactylate 8% AS, water to 100%.

The invention claimed is:

1. A concentrated base, for a detergent product or a product for personal care and hygiene, consisting of a combination of at least three surfactants selected from the group consisting of acylmethyltaurates of formula (I), alkylamidopropylbetaines of formula (II), alkyl amphoacetates of formula (III), alkyl amphodiacetates of formula (IV), alkylsulphoacetates of formula (V), acylsarcosinates of formula (VI), acyl lactylates of formulae (VII) and (VII)' and acylglutamates of formula (VIII) and water, wherein:

formula (I) is:

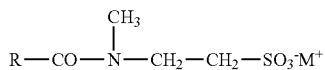
(I)

wherein R is a linear or branched, saturated or unsaturated alkyl radical, having from 3 to 30 carbon atoms and $M^+$ is $H^+$ or a cation of an organic or inorganic base;

formula (II) is:

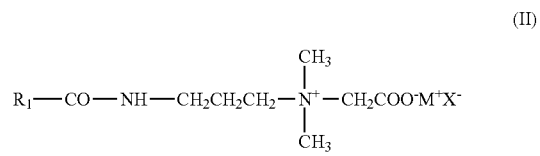
(II)

wherein $R_1$ is a saturated or unsaturated, linear or branched alkyl radical, having from 3 to 30 carbon atoms, $M^+$ is $H^+$ or a cation of an organic or inorganic base, $X^-$ is an inorganic or organic anion;

formula (III) is:

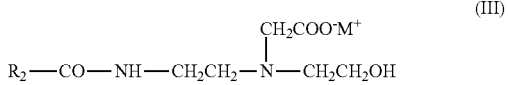
(III)

wherein $R_2$ is a saturated or unsaturated, linear or branched alkyl radical, having from 3 to 30 carbon atoms, $M^+$ is $H^+$ or a cation of an organic or inorganic base;

formula (IV) is:

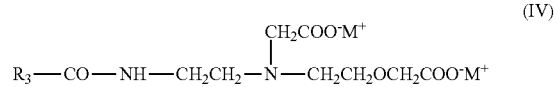
(IV)

wherein $R_3$ is a saturated or unsaturated, linear or branched alkyl radical, having from 3 to 30 carbon atoms, preferably derived from coco, $M^+$ is $H^+$ or a cation of an organic or inorganic base;

formula (V) is:

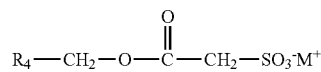
(V)

wherein $R_4$ is a saturated or unsaturated, linear or branched alkyl radical, having from 3 to 30 carbon atoms and $M^+$ is $H^+$ or a cation of an organic or inorganic base;

formula (VI) is:

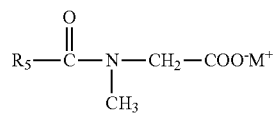
(VI)

wherein $R_5$ is a saturated or unsaturated, linear or branched alkyl radical, having from 3 to 30 carbon atoms and $M^+$ is $H^+$ or a cation of an organic or inorganic base;

formulae (VII) and (VII)' are:

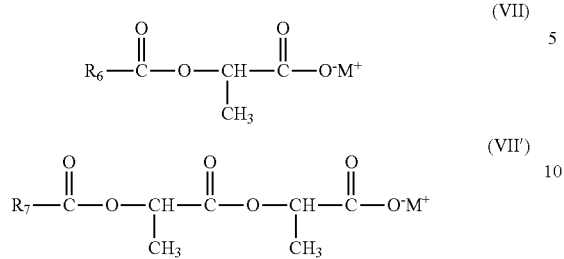

wherein $R_6$ and $R_7$ are, independently of one another, a saturated or unsaturated, linear or branched alkyl radical, having from 3 to 30 carbon atoms and $M^+$ is $H^+$ or a cation of an organic or inorganic base;
formula (VIII) is:

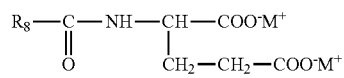

wherein $R_8$ is a saturated or unsaturated, linear or branched alkyl radical, having from 3 to 30 carbon atoms and $M^+$ is $H^+$ or a cation of an organic or inorganic base.

2. The concentrated base according to claim 1, wherein the total amount of surfactant is comprised within the range of 3% to 65% of active substance.

3. The concentrated base according to claim 1, consisting of from 1% to 25% of active substance of sodium myristoylsarcosinate of formula (a), from 1% to 25% of active substance of cocoamidopropyl betaine of formula (b), from 1% to 10% of active substance of sodium laurylsulphoacetate of formula (c), and water q.s to 100%, wherein:
formula (a) is:

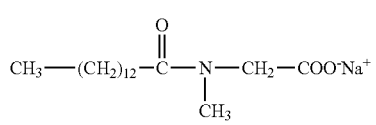

formula (b) is:

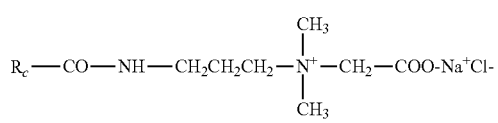

wherein $R_c$ is the mixture of alkyl radicals derived from coco, formula (c) is:

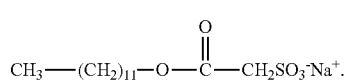

4. The concentrated base according to claim 1, consisting of from 1 to 30% of active substance of sodium cocoamphoacetate of formula (d), from 1% to 25% of active substance of sodium myristoylsarcosinate of formula (a), from 1% to 10% of active substance of sodium laurylsulphoacetate of formula (c) and water q.s. to 100%, wherein
formula (d) is:

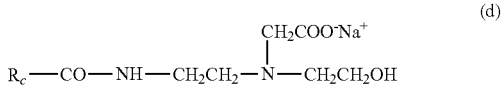

wherein $R_c$ is the mixture of alkyl radicals derived from coco, and formulae (a) and (c) are as follows:

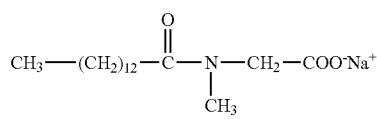

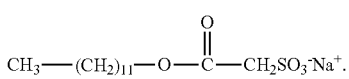

5. The concentrated base according to claim 1, consisting of from 1% to 25% of active substance of sodium myristoylglutamate of formula (e), from 1% to 25% of active substance of cocoamidopropyl betaine of formula (b), from 1% to 10% of active substance of sodium laurylsulphoacetate of formula (c) and water q.s. to 100%, wherein
formula (e) is:

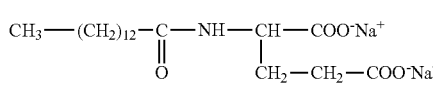

and formulae (b) and (c) are as follows:

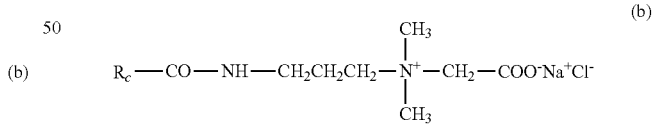

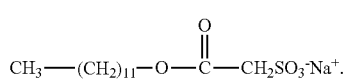

6. The concentrated base according to claim 1, consisting of from 1 to 30% of active substance of sodium cocoamphoacetate of formula (d), from 1% to 25% of active substance of sodium myristoylglutamate of formula (e), from 1% to 10% of active substance of sodium laurylsulphoacetate of formula (c) and water q.s. to 100%, wherein formula (d) is as follows, formula (e) is as follows, and formula (c) is as follows:

    (d)

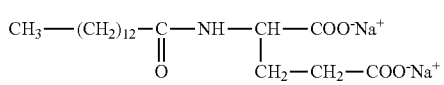    (e)

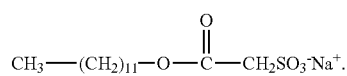    (c)

7. The concentrated base according to claim 1, consisting of from 1% to 25% of active substance of sodium myristoylglutamate of formula (e), from 1% to 25% of active substance of cocoamidopropyl betaine of formula (b), from 1% to 10% of active substance of sodium myristoylsarcosinate of formula (a), from 1% to 10% of active substance of sodium cocoyl methyltaurate of formula (f) and water q.s. to 100%, wherein formula (f) is:

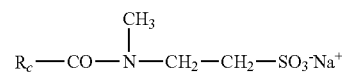    (f)

wherein $R_c$ is the mixture of alkyl radicals derived from coco, and formula (e) is as follows, and formulae (b) and (a) are as follows:

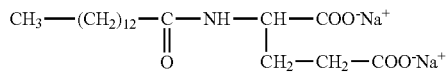    (e)

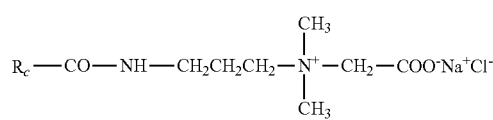    (b)

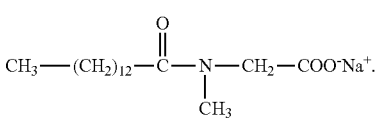    (a)

8. The concentrated base according to claim 1, consisting of from 1 to 30% of active substance of sodium cocoamphoacetate of formula (d), from 1% to 15% of active substance of sodium myristoylglutamate of formula (e), from 1% to 10% of active substance of sodium myristoylsarcosinate of formula (a), from 1% to 10% of active substance of sodium cocoyl methyltaurate of formula (f) and water q.s. to 100%, wherein formula (d) is as follows, formula (e) is as follows, formula (a) is as follows and formula (f) is as follows:

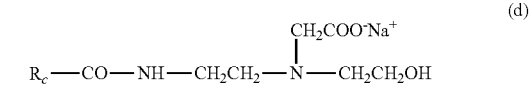    (d)

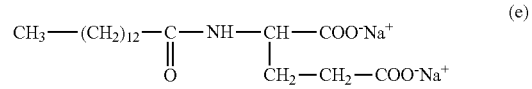    (e)

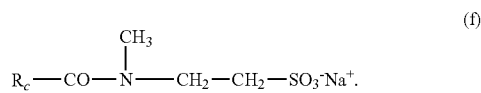    (f)

9. The concentrated base according to claim 1, consisting of from 1% to 25% of active substance of sodium myristoylsarcosinate of formula (a), from 1% to 25% of active substance of cocoamidopropyl betaine of formula (b), from 1% to 15% of active substance of sodium lauroyl lactylate of formula (g) and water q.s. to 100%, wherein formula (g) is:

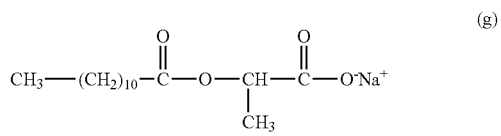    (g)

and formulae (a) and (b) are as follows:

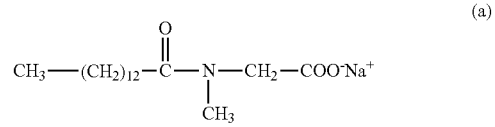    (a)

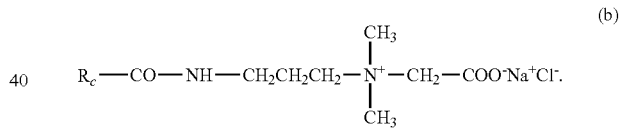    (b)

10. The concentrated base according to claim 1, consisting of from 1 to 30% of active substance of sodium cocoamphoacetate of formula (d), from 1% to 25% of active substance of sodium myristoylsarcosinate of formula (a), from 1% to 15% of active substance of sodium lauroyl lactylate of formula (g) and water q.s. to 100%, wherein formula (d) is as follows, formula (a) is as follows and formula (g) is as follows:

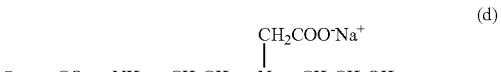    (d)

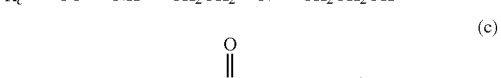    (c)

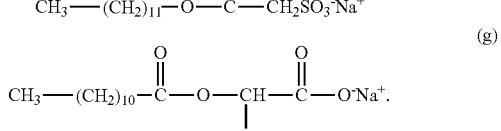    (g)

11. The concentrated base according to claim 1, consisting of from 1% to 25% of active substance of sodium myristoyl glutamate of formula (e), from 1% to 25% of active substance of cocoamidopropyl betaine of formula (b), from 1% to 15% of active substance of sodium lauroyl lactylate of formula (g) and water q.s. to 100%, wherein formula (e) is as follows, formula (b) is as follows and formula (g) is as follows:

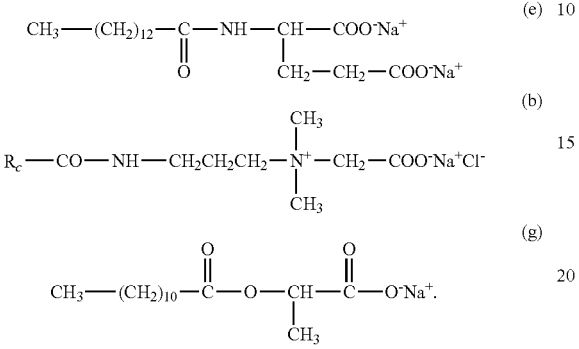

12. The concentrated base according to claim 1, consisting of from 1 to 30% of active substance of sodium cocoamphoacetate of formula (d), from 1% to 25% of active substance of sodium myristoyl glutamate of formula (e), from 1% to 15% of active substance of sodium lauroyl lactylate of formula (g) and water q.s. to 100%, wherein formula (d) is as follows, formula (e) is as follows and formula (g) is as follows;

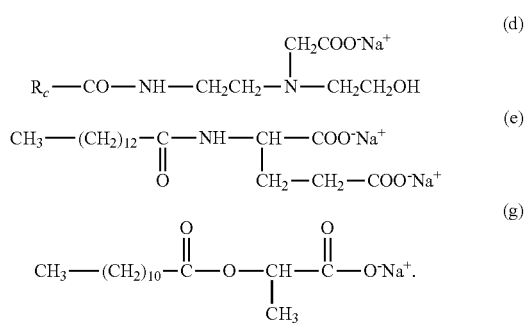

13. A detergent product consisting of a concentrated base according to claim 1 and suitable additives.

14. A product for personal care or hygiene consisting of a concentrated base according to claim 1 and suitable additives.

* * * * *